United States Patent [19]

Esteve Subirana

[11] 4,267,334
[45] May 12, 1981

[54] 6-METHOXY-2-ACETHYLNAPHTHALENE OXIMES

[75] Inventor: Antonio Esteve Subirana, Barcelona, Spain

[73] Assignee: Productos Esteve Internacional S.A., Barcelona, Spain

[21] Appl. No.: 59,249

[22] Filed: Jul. 20, 1979

[30] Foreign Application Priority Data

Aug. 2, 1978 [FR] France ............................... 78 22836

[51] Int. Cl.³ .................. C07D 241/04; C07D 207/09; C07C 131/00
[52] U.S. Cl. ............................ 546/206; 260/326.5 C; 424/274; 424/250; 424/327; 564/256
[58] Field of Search ................. 260/566 AE, 326.5 C; 546/206

[56] References Cited

U.S. PATENT DOCUMENTS 3,963,778   6/1976   Schütz et al. ................. 260/566 AE

Primary Examiner—Anton H. Sutto
Assistant Examiner—D. B. Springer
Attorney, Agent, or Firm—Dressler, Goldsmith, Shore, Sutker & Milnamow, Ltd.

[57] ABSTRACT

The invention concerns 6-methoxy-2-acetylnaphthalene oxime derivatives of the general formula

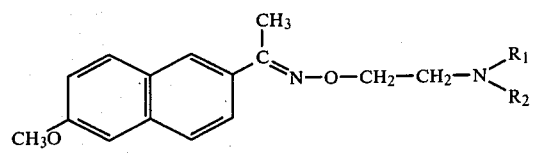

in which $R_1$ and $R_2$ each represent a lower alkyl radical, or form, in association with the nitrogen atom to which they are linked, a saturated heterocyclic group, and the acid addition salts thereof with physiologically acceptable acids. These derivatives have analgesic, antipyretic and anti-inflammatory activity and can be made up into pharmaceutical compositions in tablet, capsule, suppository and the like forms. The derivatives of the invention may be prepared by reacting the corresponding 2-acetyl-6-methoxynaphthalene oximes with an appropriate substituted halogeno-ethylamine.

11 Claims, No Drawings

6-METHOXY-2-ACETHYLNAPHTHALENE OXIMES

The present invention concerns new derivatives of 6-methoxy-2-acetylnaphthalene oxime, their preparation and their application as medicaments.

The new derivatives, the object of the present invention, are the general formula I

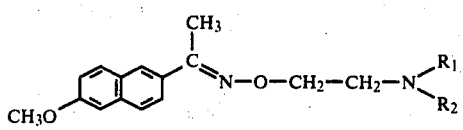

in which $R_1$ and $R_2$ each represent a lower alkyl radical, preferably with $C_1$ to $C_4$, or form, in association with the nitrogen atom to which they are linked, a saturated heterocyclic group.

The present invention also provides the addition salts of physiologically acceptable acids, such as the halogenohydrates and especially the chlorhydrates, of the derivatives of formula I.

The derivatives of formula I and their acid addition salts present valuable pharmacological, analgesic, antipyretic and anti-inflammatory properties and the invention therefore also resides in the application of these compounds as medicaments, as well as to pharmaceutical compositions containing them as an active ingredient.

The preferred derivatives of the invention are those of formula I in which $R_1$ and $R_2$ are identical and represent a methyl or ethyl radical, preferably an ethyl radical, or in which $R_1$ and $R_2$ form, in association with the nitrogen atom to which they are linked, a pyrrolidino or piperidino group, preferably pyrrolidino.

The present invention also relates to the preparation of the derivatives of general formula I. According to the method of the invention, the oxime of 2-acetyl-6-methoxy-naphthalene of formula II

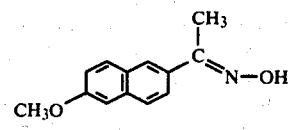

is reacted with a substituted halogeno-ethylamine of general formula III

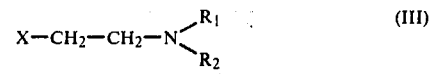

in which:

X represents a halogen atom, especially chlorine, and $R_1$ and $R_2$ each represent a lower alkyl radical, preferably with $C_1$ to $C_4$, or form, in association with the nitrogen atom to which they are linked, a saturated heterocyclic group.

Hereinafter, as a non-limiting example, the preparation of 6-methoxy-2-acetylnaphthalene-O-(2-dimethylaminoethyl)oxime in the free base form and in the halogenohydrate form will be described in more detail.

EXAMPLE 1

6-methoxy-2-acetylnaphthalene-O-(2-dimethylaminoethyl)oxime 21.5 g (0.1 mole) of the oxime of 2-acetyl-6-methoxynaphthalene, 2.5 g (0.1 mole) of sodium hydride, and 200 ml of anhydrous dioxane are added in a 500 ml Erlenmeyer flask equipped with a stirring device, a refrigerant and a tube of calcium chloride.

The temperature is maintained at 70° C. for 3 hours and 0.11 mole of dimethylated chloroethylamine are then added.

The temperature is maintained at 70° C. for 12 hours, cooling off is allowed, and the contents are poured into 2 liters of water. A precipitate is formed which is filtered and then washed with distilled water.

By recrystallisation, for example in methanol, the 6-methoxy-2-acetylnaphthalene-O-(2-dimethyl-aminoethyl)oxime in the form of the free base (Melting Point 93°–96° C.) is obtained.

To obtain the corresponding halogenohydrate, for example the chlorhydrate, the free base is reacted with ethanol saturated with a halogenohydric acid, for example hydrochloric acid, and then evaporated under vacuum. Then, recrystallisation, for example in acetonitrile, is carried out.

The chlorhydrate thus obtained has a melting point of 238° to 240° C.

EXAMPLES 2 to 4

Operating in a manner identical to that described in Example 1, using the equivalent substituted chloroethylamine, the diethyl, pyrrolidino and piperidino derivatives are obtained.

Table I tabulates some of the physicochemical constants of these derivatives, in particular the crystallisation solvents, the melting points and the characteristic peaks of the NMR spectra.

TABLE I

| Ex. No | R | Melting Point base | Crystallisation Solvent | Melting Point HCl | Crystallisation Solvent HCl | Yield | NMR* | ANALYSIS % (Base) | | |
|---|---|---|---|---|---|---|---|---|---|---|
| | | | | | | | | | C | H | N |
| 1 | —N(CH₃)CH₃ | 93–96° C. | MeOH | 238–40° C. | CH₃CN | 67% | de 8,28 a 7,28 (6H,m);5,82 (2H,t 4,28 (3H,s); (2H,t); 3,78 (9H,8); 4,42 | Calculated Found | 78,97 79,17 | 8,15 8,26 | 5,14 4,98 |

TABLE I-continued $$\text{CH}_3\text{O} - \text{naphthalene} - \underset{\underset{CH_3}{|}}{C} = N - O - CH_2 - CH_2 - R$$

| Ex. No | R | Melting Point base | Crystallisation Solvent | Melting Point HCl | Crystallisation Solvent HCl | Yield HCl | NMR* | ANALYSIS % (Base) | | |
|---|---|---|---|---|---|---|---|---|---|---|
| | | | | | | | | C | H | N |
| 2 | $-N\begin{smallmatrix}CH_2-CH_3\\CH_2-CH_3\end{smallmatrix}$ | 54–55° C. | EtOH/H₂O | 191–3°C. | CH₃CN | 47% | de 8,2 a 7,2(6H,m); 5,85 (2H,t) 4,25 (3H,s); 4,68 (8H,m); 3,8 (3H,s); 1,0 (3H,t) | Calculated Found | 76,00  8,73  4,66<br>75,89  8,63  4,58 | |
| 3 | $-N\bigcirc$ (pyrrolidine) | 88–91° C. | EtOH/H₂O | 225–7°C. | C₃CN ou EtOH | 53% | de 8,2 a 7,25 (6H,m); 5,8 (2H,t) 4,25 (3H,s) ; 3,3 (2H,t); 3,53 (4H,m); 3,88 (3H,s); 2,3 (4H,m) | Calculated Found | 74,46  8,10  4,69<br>76,31  7,89  4,60 | |
| 4 | $-N\bigcirc$ (piperidine) | 82–83° C. | MeOH/H₂O | 220–1° C. | CH₃CN | 61% | de 8,2 a 7,2 (6H,m); 5,8 (2H,t) 4,25 (3H,s); 3,82 (2H,t); 3,65 (4H,m), 3,8 (3H,s); 2,55 (6H,m) | Calculated Found | 76,87  8,39  4,48<br>76,74  8,41  4,50 | |

*Solvent CCL₄ Internal reference, TMS, displacement in δ
m = multiplet,
s = singlet,
t = triplet.

Analgesic activity

The analgesic activity of the derivatives of general formula I has been determined using male mice of a weight between 20 and 25 g. The product to be tested is administered orally in suspension in 5% gum arabic by means of an oesophageal probe. The volume of the solution administered is 25 ml/kg and the concentration of the product tested is changed according to the dose administered.

Pain is caused in the animals by means of an intraperitoneal injection of 0.2 ml/20 g of acetylcholine bromide solution at a concentration of 0.32 mg/ml. Five minutes before the administering of the product tested, the acetylcholine is injected into a batch of 5 mice. The product to be tested is then administered, and the injection of acetylcholine is carried out again after 20, 40, 80, 120 and 160 minutes. Every time, the number of contortions per injection of acetylcholine during five minutes is counted.

The analgesic activity is calculated by means of the following formula:

$$It = 100 - (Nt/No).100 = 100(1 - Nt/No)$$

where
It = inhibition of pain after t minutes
No = Number of contortions before the administration of the product
Nt = Number of contortions after t minutes from the administration of the product.

Several doses of each product are administered in order to determine the fifty percent analgesic dose (AD-50).

With each of these doses, It is calculated at times 20, 40, 80, 120 and 160 minutes. The mean of these five values of It for each dose is taken as analgesic effect. The analgesic effects are represented graphically as a function of the logarithm of the corresponding dose.

From this curve, the fifty analgesic dose, that is to say the dose which produces a fifty percent analgesic effect, is obtained.

The results obtained for the derivatives of Examples 1 to 4 are indicated in Table II.

Acute toxicity

The acute oral toxicity is determined with mice of 20 to 25 g weight by using batches of 6 animals. Several doses in geometric progression are administered. The time of observation is 72 hours. The fifty percent lethal doses (LD-50) is calculated graphically by means of logarithmic-probabilistic paper.

The results obtained for the derivatives of Examples 1 to 4 are indicated in Table II hereinafter.

TABLE II

| Example No | DERIVATIVE | Doses in mg/kg | |
|---|---|---|---|
| | | AD – 50 | LD – 50 |
| 1 | 6-methoxy-2-acetylnaphthalene-0-(2-dimethyl-amino-ethyl) oxime, chlorhydrate | 40 | 336 |
| 2 | 6-methoxy-2-acetylnaphthalene-0-(2-diethyl-amino-ethyl) oxime, chlorhydrate | 17,5 | 490 |
| 3 | 6-methoxy-2-acetylnaphthalene-0-(2-pyrrolidino-ethy) oxime, chlorhydrate | 35 | 1394 |
| 4 | 6-methoxy-2-acetylnaphthalene-0-(2-piperidino-ethyl) oxime, chlorhydrate | 22 | 254 |

Anti-inflammatory activity

The anti-inflammatory activity is determined with male rats of Sprague-Dawley stock. An oedema is caused in the paw by subplantar injection of a solution of 1% carragheenin. The volume of the paw is measured before the oral administration of the product, and after two and five hours, with a plethysometer. The anti-inflammatory activity is calculated with respect to a reference batch. The results obtained for the derivative of Example 3 are indicated in Table III hereinafter.

TABLE III

| Example No. | DERIVATIVE | Dose (Mg/Kg) | Anti-inflammatory activity 2 hours | 5 hours |
| --- | --- | --- | --- | --- |
| 3 | 6-methoxy-2-acetyl-naphthalene-0-(2-pyrrolidinoethyl) oxime, chlorhydrate | 175 | 38% | 39% |

Taking into account their good pharmacodynamic properties, the derivatives of general formula I are hence capable of being used in veterinary and/or human medecine, as analgesic, antipyretic and anti-inflammatory agents.

Pharmaceutical compositions which contain, according to the invention, in addition to a pharmaceutically acceptable support, at least one derivative of general formula I have a very large field of therapeutic application and can be utilised especially in traumatology, surgery, rheumatology, odontostomatology, oto-rhino-laryngology, pneumology, cardiology, gynaecology and urology. These pharmaceutical compositions can be, for example, utilised for the treatment of various manifestations of pain, headaches, migraines, toothache, neuralgias, menstrual pains, inflammatory rheumatisms, arthritic pains, feverish states, colds, influenzas and seasonal infections.

As human therapeutic, the dose proposed for the derivatives of the present invention is approximately comprised between 100 and 500 mg/day, administered for example in the form of tablets, capsules or suppositories.

As examples, three particular gallenic forms of the derivatives, the objects of the present invention, will be indicated.

| Example of formula per tablet | |
| --- | --- |
| 6-methoxy-2-acetylnaphthalene-0-(2-pyrrolidino-ethyl)oxime, chlorhydrate | 100 mg |
| Amidon | 50 mg |
| Primogel | 10 mg |
| Lactose | 53 mg |
| Polyvinylpyrrolidone | 10 mg |
| Magnesium stearate | 2 mg |
| tablet weight | 225 mg |

| Example of formula per capsule | |
| --- | --- |
| 6-methoxy-2-acetylnaphthalene-0-(2-pyrrolidino-ethyl)oxime, chlorhydrate | 100 mg |
| Avicel ph 102 | 76 mg |
| Aerosil-200 | 1.5 mg |
| Magnesium stearate | 2.5 mg |
| Capsule weight | 180 mg |

| Example of formula per suppository | |
| --- | --- |
| 6-methoxy-2-acetylnaphthalene-0-(2-pyrrolidino-ethyl)oxime, chlorhydrate | 0.2 g |
| Monolene | 1.8 g |
| | 2.0 g |

What is claimed is:

1. A 6-methoxy-2-acetylnaphthalene oxime derivative of the formula

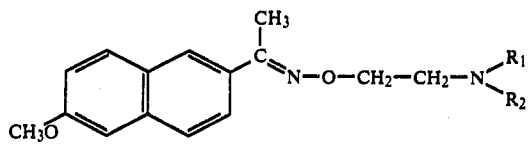

in which $R_1$ and $R_2$ each represent a lower alkyl radical of from 1 to 4 carbon atoms, or form, in association with the nitrogen atom to which they are linked, a pyrrolidino or piperidino group and the acid addition salts thereof with physiologically acceptable acids.

2. A derivative as claimed in claim 1, wherein $R_1$ and $R_2$ each represent a methyl or an ethyl radical.

3. A chlorhydrate salt of a derivative as claimed in claim 1.

4. 6-methoxy-2-acetylnaphthalene-O-(2-diethylaminoethyl)oxime.

5. The chlorhydrate of the compound claimed in claim 4.

6. 6-methoxy-2-acetylnaphthalene-O-(2-pyrrolidinoethyl)oxime.

7. The chlorhydrate of the compound claimed in claim 6.

8. 6-methoxy-2-acetylnaphthalene-O-(2-dimethylaminoethyl)oxime.

9. The chlorhydrate of the compound claimed in claim 8.

10. 6-methoxy-2-acetylnaphthalene-O-(2-piperidinoethyl)oxime.

11. The chlorhydrate of the compound claimed in claim 10.

* * * * *

UNITED STATES PATENT OFFICE
CERTIFICATE OF CORRECTION

Patent No. 4,267,334      Dated May 12, 1981

Inventor(s) Antonio Esteve Subirana

It is certified that error appears in the above-identified patent and that said Letters Patent are hereby corrected as shown below:

In Table I at the bottom of the first page, bridging columns 1 and 2:

in the "NMR*" column - second line, insert --3,42-- after "(3H,s)."

in the "NMR*" column - third line- after "(9H,8)", delete "4,42"

Signed and Sealed this

Thirteenth Day of October 1981

[SEAL]

Attest:

Attesting Officer

GERALD J. MOSSINGHOFF

Commissioner of Patents and Trademarks

UNITED STATES PATENT OFFICE
CERTIFICATE OF CORRECTION

Patent No. 4,267,334                    Dated May 12, 1981

Inventor(s)  Antonio Esteve Subirana

It is certified that error appears in the above-identified patent and that said Letters Patent are hereby corrected as shown below:

Title page, first column in line designated "[73]", after "Assignee:", delete "Productos Esteve International S.A., Barcelona, Spain" and substitute --Provesan S.A., Geneva, Switzerland.--

Signed and Sealed this

Seventh Day of June 1983

[SEAL]

Attest:

DONALD J. QUIGG

Attesting Officer    Acting Commissioner of Patents and Trademarks